United States Patent [19]

LoPiano

[11] 4,236,513
[45] Dec. 2, 1980

[54] PULSED OXYGEN CHAMBER

[76] Inventor: Rocco W. LoPiano, 26 Journal Sq., Jersey City, N.J. 07306

[21] Appl. No.: 31,053

[22] Filed: Apr. 18, 1979

[51] Int. Cl.³ .............................................. A61M 13/00
[52] U.S. Cl. ...................................... 128/184; 128/40; 128/299
[58] Field of Search .................... 128/38–40, 128/60, 64, 297, 299, 184, 204

[56] References Cited

U.S. PATENT DOCUMENTS

| 2,113,253 | 4/1938 | Gray | 128/38 |
| 2,134,646 | 10/1938 | Sauzedde | 128/38 |
| 3,345,985 | 10/1967 | Fisher | 128/204 |
| 3,712,298 | 1/1973 | Snowdon et al. | 128/40 |
| 4,003,371 | 1/1977 | Fischer | 128/184 |

Primary Examiner—Lawrence W. Trapp
Attorney, Agent, or Firm—DeLio and Montgomery

[57] ABSTRACT

A treatment chamber for a human extremity specially adapted for use with a pulsed or hyperbaric oxygen supply, the chamber comprising upper and lower sections adapted to be sealingly clamped together and provided at one end with a demountable annular sleeve, which fits sealingly against the sides of a patient's extremity and against a chamber end closure element.

3 Claims, 9 Drawing Figures

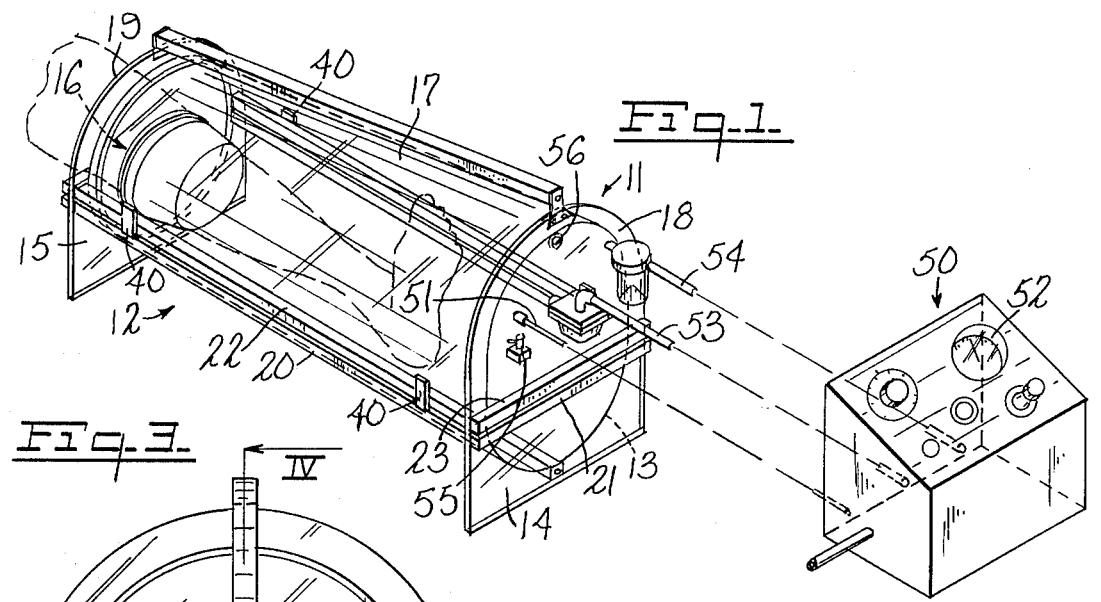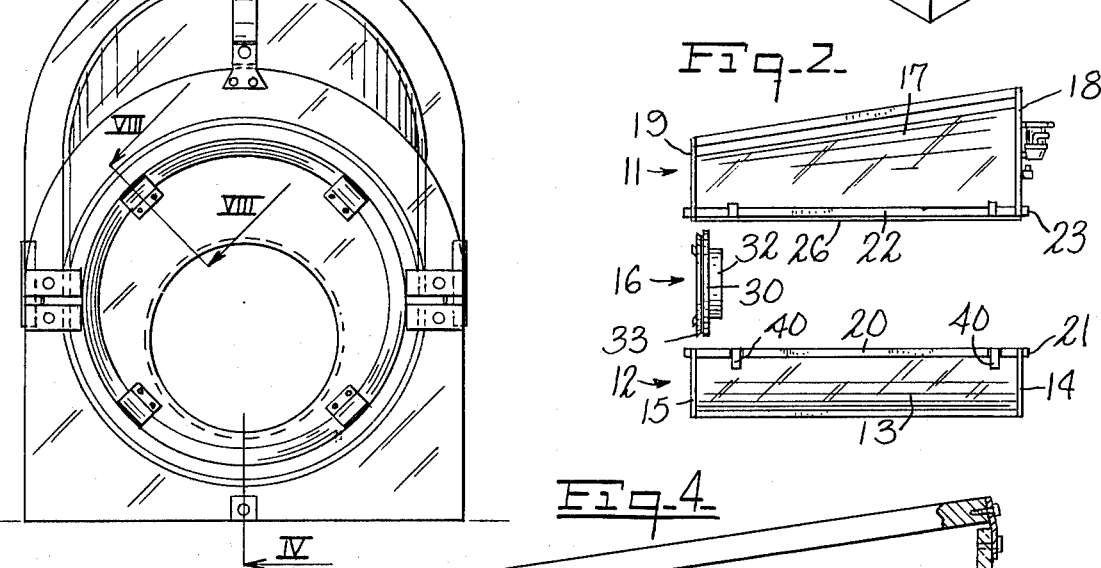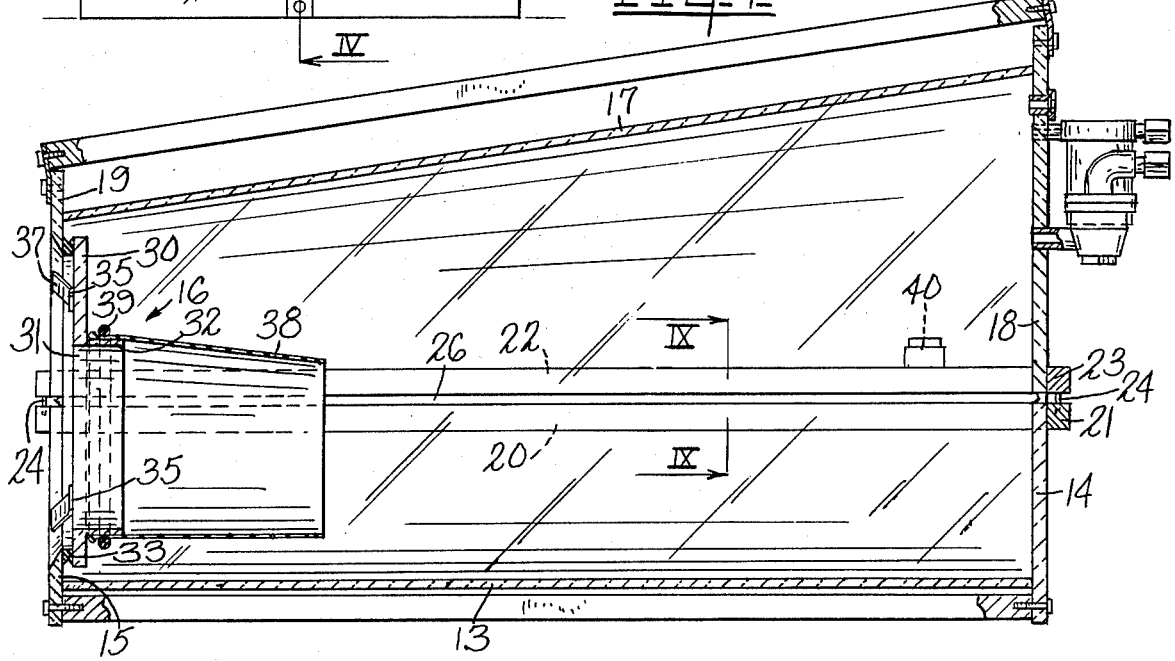

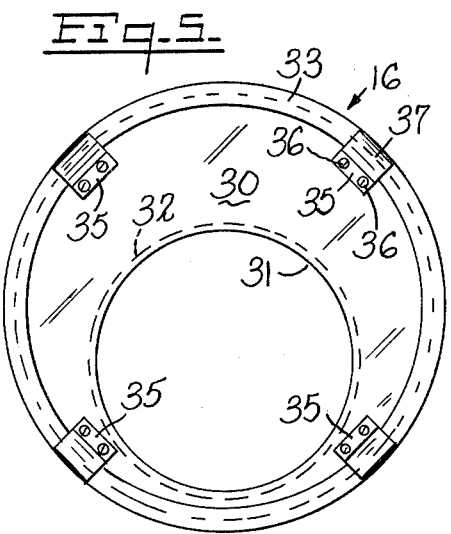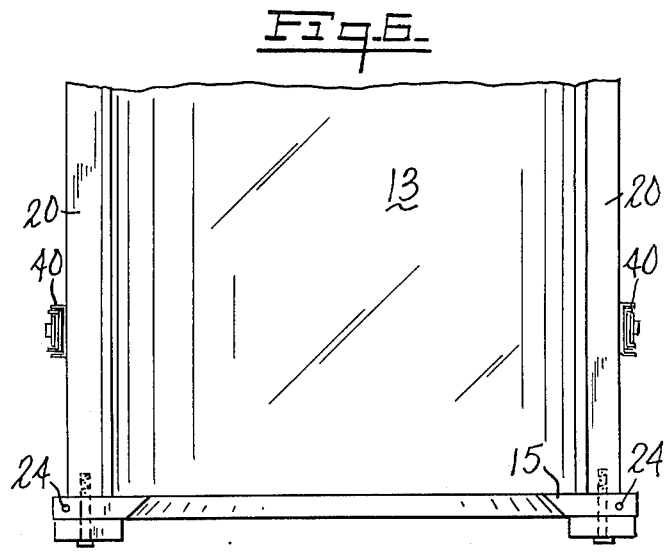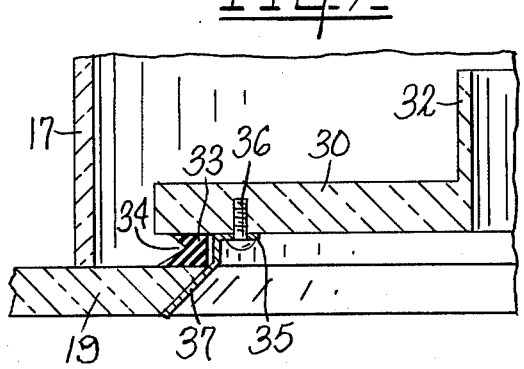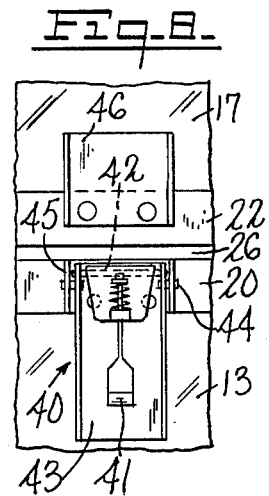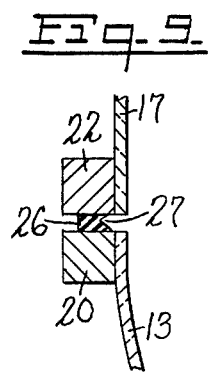

PULSED OXYGEN CHAMBER

This invention relates to a controlled pressure oxygen treatment system which includes a chamber adapted to receive and enclose a human extremity and a gas (oxygen) supply circuit, with controls, adapted to supply the gas to the chamber automatically in pulses of predetermined frequency, duration and pressure. A modified form of chamber is disclosed in application Ser. No. 31,052 filed of even date herewith.

It is known to use hyperbaric oxygen topically to treat pressure sores, wounds, skin lesions, decubiti and ulcers, chambers for this purpose being shown and described in Fischer U.S. Pat. Nos. 3,744,491, July 10, 1973 and 4,003,371, Jan. 18, 1977. In these chambers the flow of oxygen past the enclosed leg or arm of a patient is continuous, at a low constant pressure of 22 mmHg, for example, and is continued for several hours a day (preferably six to eight) over periods which may average several weeks, to aid in the healing of various lesions.

Studies have now revealed that the treatment time for ulcerations and lesions originating from various etiologies can be substantially reduced by resorting to the use of pulsating oxygen treatment, particularly in the present oxygen chamber. Actual trials in a leading hospital have shown a median healing time of 19 days, substantially less than the time required for more conventional treatment.

It is accordingly an object of the present invention to provide a treatment chamber for a human extremity specially adapted for use with a pulsed oxygen supply. Suitable oxygen supply circuits are disclosed in Fischer Applications Serial No. 858,960 and Ser. No. 52,488, filed June 27, 1979.

It is another object of the invention to provide such a chamber which is designed to use the hospital oxygen supply, to which it can be connected and from which it can be removed in seconds.

It is a further object of the invention to provide a chamber which is of simple construction, sturdy and easily cold-sterilized.

It is another object of the invention to provide certain improvements in the form, construction and arrangement of the several parts whereby the above-named and other objects of the invention can readily be achieved.

The invention accordingly comprises the features of construction, combination of elements and arrangement of parts which will be exemplified in the construction hereinafter set forth, and the scope of the invention will be indicated in the claims.

A practical embodiment of the invention is shown in the accompanying drawings wherein:

FIG. 1 represents a somewhat diagrammatic perspective view of the chamber and control station;

FIG. 2 represents an exploded side elevation of the chamber;

FIG. 3 represents an elevation of the inlet end of the chamber;

FIG. 4 represents a vertical section on the line IV—IV of FIG. 3;

FIG. 5 represents a detail end elevation of the sealing sleeve and hub;

FIG. 6 represents a detail plan view of the inlet end of the lower chamber section, parts being broken away;

FIG. 7 represents a detail section on the line VII—VII of FIG. 5;

FIG. 8 represents a detail elevation of a hold-down clamp; and

FIG. 9 represents a vertical section on the line IX—IX of FIG. 4.

Referring to the drawings, and particularly FIGS. 1 to 9, the oxygen chamber itself comprises upper and lower portions 11, 12, the lower portion 12 including a semi-cylindrical trough 13 having a rectangular lower end wall 14 at the closed end of the chamber and a corresponding rectangular wall 15 at the inlet end, cut away on a semi-circular arc and beveled to receive the ring-sleeve assembly 16. The upper portion 11 has a main wall 17 which is also basically semi-cylindrical but is slanted upward toward the closed end to give the chamber increased height (e.g., to accommodate the patient's foot, as shown in FIG. 1). The end wall 18 at the closed end has a horizontal bottom edge, matching the top edge of the lower end wall 14, and curved side and top edges matching the curvature of the wall 17. At the inlet end the wall 19 is arcuate and its radially inner edge is complementary to the semi-circular arc in the wall 15, said inner edge being similarly beveled.

The upper edges of the trough 13 and end wall 14 are reinforced by frame elements 20 and 21, respectively, which may suitably be rectangular (e.g., square) in cross-section and are cemented or otherwise secured along the respective edges. The lower edges of the main wall 17 and upper end wall 18 are likewise reinforced by similar frame elements 22 and 23, respectively, similarly secured. Accurate registry of the upper chamber portion 11 on the lower portion 12 is assured by the provision of pilot pins 24 on the upper portion adapted to engage in holes in the lower portion.

Hermetic sealing between the upper and lower portions is effected by means of the gasket 26 (FIG. 9), of elastomeric material, rectangular in cross-section with a groove 27 along its inner face, whereby the sealing effect is increased with the rise of gas pressure within the chamber.

The ring-sleeve assembly 16 comprises a flat round plate 30 having an eccentrically located circular opening 31. The annular lip 32 projects inwardly from the periphery of the opening 31 and an annular gasket 33 is mounted adjacent the periphery of the plate on the outer surface thereof. In the cross-sectional profile the gasket 33 is like the gasket 26, with a groove 34 around its radially outward surface (FIG. 7). Four angular brackets 35 are secured, as by screws 36, to the outer face of the plate 30 to 90° intervals, each being 45° from vertical when the opening 31 is in its lowest position, as clearly shown in FIG. 3, the projecting portion 37 of each bracket being angled to rest against the beveled edges of the semi-circular cut-outs in the walls 15 or 19, respectively.

The ring-sleeve assembly is completed by a sleeve 38 which is conical with its wider end designed for placement over the ring lip 32 where it is firmly held by means of the elastic retainer band 39. Sleeves are preferably provided in a range of sizes such that the smaller end of the selected sleeve will fit snugly—not tightly—on the limb to be treated. Rings also may vary in the diameter of the interior opening, diameters of five inches and six inches being appropriate, and the sleeves being sized accordingly. The sleeves are of flexible, somewhat elastic, sterilizable material such as a surgical quality latex compound.

The toggle-type latch 40 shown in detail in FIG. 8 includes a spring mounted hook 41 pivoted at 42 on the short end of the lever 43 which is pivotally mounted at 44 on brackets 45 fixed to the frame element 20. The hook 41 is engageable with the keeper 46 on the frame element 22 and is tightened in a conventional manner by swinging the lever 43 upward 180°. Four such latches are usually provided, two on each side, in the locations indicated in FIGS. 1 to 6.

The closed end 18 of the chamber is shown as being provided with means for connection to the circuit control box 50 which is fully disclosed and explained in the Fischer Application Ser. No. 52,488, previously referred to, namely, a sensing conduit 51 connected to a pressure gauge 52, a gas supply conduit 53 and an exhaust valve power conduit 54. A manually operated vent is shown at 55 and an over-pressure relief vent is shown at 56. If the chamber is used with the electrically actuated system of Fischer Application Ser. No. 858,960 only two conduits will be used between the chamber and the control box, as disclosed and explained in said application.

In use, for the treatment of a lesion on a limb (e.g., leg), a temporary dressing is applied to the lesion, for protection; the affected extremity is inserted through a ring-sleeve assembly of the correct size; the ring-sleeve assembly is moved to a position such that the free edge of the sleeve is spaced from the lesion, so that the latter will be completely exposed during treatment; care is taken to see that the narrowest part of the ring (preferably marked in some manner) is at the bottom, as in FIG. 3.

With the patient and the lower portion 12 of the chamber suitably juxtaposed, the extremity is lifted and the ring is placed carefully in engagement with the arcuate cut-out in the end wall 15, the angled portions 37 of the two lower brackets 35 being engaged with the beveled edge of the cut-out and the outer surface of the gasket 33 resting against the inner surface of the wall 15. After removing the temporary dressing from the lesion, the upper portion 11 of the chamber is set in place by first carefully engaging the beveled edge of the cut-out in wall 19 with the two upper brackets 35 and then lowering the upper portion into complete peripheral sealing engagement with a lower portion, in a position determined by the guide pins 29 as well as by the ring 30 and brackets 35. A gas tight seal is effected by actuating the latches 40.

To assure proper operation of the chamber, the entire sleeve portion of the extremity should always be positioned inside the chamber. Positive pressure exerts a constant force trying to push the extremity out of the chamber. This may result in external ballooning of the sleeve with resulting loss of hermetic seal. Usually the weight of the extremity suffices to keep it stationary inside the chamber. In debilitated patients with decreased muscle tonus or muscle wastings, a six-pound sand bag (butterfly type) placed across the thigh secures steady anchoring of the extremity.

After treatment has been terminated, the disassembly of the chamber and separation of same from the patient involves merely:

Releasing the latches and removing the upper portion 11.

Applying temporary dressing to the lesion.

Lifting the extremity so that the lower portion 12 can be moved.

Carefully remove the ring-sleeve assembly and check condition of skin under the sleeve.

Apply regular dressing to the lesion.

The sleeves are disposable with an anticipated life of two to three days after which time they should be discarded and replaced. Soiled or damaged sleeves should be immediately discarded. To avoid the possibility of cross contamination, the ring should be used only on a single patient during an entire course of treatment, otherwise sterilization is required.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawing shall be interpreted as illustrative and not in a limiting sense.

What I claim is:

1. A closable chamber for use in gas treatment of a human limb comprising separable lower and upper portions and a ring-sleeve assembly, the lower portion including an elongated upwardly facing trough having a closed end wall and a partially cut away end wall, the upper portion including an elongated downwardly facing trough having a closed end wall and a partially cut away end wall, each of the upper portion end walls being complementary to the respective lower portion end walls and the cut away walls having beveled edges which cooperate to define a substantially circular opening, the lower and upper portions having matching peripheral edges, upwardly and downwardly facing, respectively, and a vertically compressible sealing gasket being located between said edges, and the ring-sleeve assembly being provided with means engageable with the beveled edges of the circular opening and a horizontally compressible sealing gasket engageable with the cut away walls.

2. A closable chamber according to claim 1 wherein at least one of the gaskets is substantially rectangular in cross-section and longitudinally grooved along its side facing the interior of the chamber.

3. A closable chamber according to claim 2 wherein each gasket is substantially rectangular in cross-section and longitudinally grooved along its side facing the interior of the chamber.

* * * * *